United States Patent
Sturaro et al.

(12)

(10) Patent No.: US 7,029,686 B2
(45) Date of Patent: Apr. 18, 2006

(54) **VARIANTS OF *PHLEUM PRATENSE* ALLERGENIC PROTEINS**

(75) Inventors: Monica Sturaro, Rome (IT); Angelo Viotti, Rome (IT); Paolo Falagiani, Milan (IT); Giovanni Mistrello, Rome (IT); Daniela Roncarolo, Rome (IT); Stefania Zanotta, Rome (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 521 days.

(21) Appl. No.: 09/949,888

(22) Filed: Sep. 12, 2001

(65) Prior Publication Data

US 2002/0064530 A1 May 30, 2002

(30) Foreign Application Priority Data

Sep. 12, 2000 (IT) .................... MI2000A1987

(51) Int. Cl.
*A61K 39/35* (2006.01)

(52) U.S. Cl. .................. 424/275.1; 530/370; 530/868
(58) Field of Classification Search .............. 530/370, 530/868; 424/275.1
See application file for complete search history.

*Primary Examiner*—Patrick J. Nolan
(74) *Attorney, Agent, or Firm*—Young & Thompson

(57) ABSTRACT

Hypoallergenic variants of the major allergen Ph1 p 1 of *Phleum pratense* plants and their use in the therapy of the allergic diseases is disclosed.

8 Claims, 2 Drawing Sheets

Inhibition of IgE binding to the allergen Phl p 1 (ELISA)

SEQUENCE LISTING

<160> NUMBER OF SEQ ID NOS: 2

<210> SEQ ID NO 1
<211> LENGTH: 720
<212> TYPE: DNA
<213> ORGANISM: Phleum pratense

<400> SEQUENCE: 1

```
atccccaagg ttcccccggg tccgaacatc acggcgacct acggcgacaa gtggctcgac      60
gcgaagagca catggtacgg cgcgccgacc ggcgccggtc ccgcggacaa cggcggcgct     120
tgcgggtacg cggatgtgga cgcgcccccg ttcagcggca tgaccggctg cggcaacacc     180
cccatcttca gtccggacg cggctgcggc tcctgctttg agatcaagtg caccaagccc      240
gaggcctgct ctggcgagcc cgtggtagtc cacatcaccg acgacaacga ggagcccatc     300
gccccctacc acttcgacct ctccgccac gcgttcgggg cgatggccaa gaagggcgat      360
gagcagaagc tgcgcagcgc cggcgagctg agctccagt tccggcgcgt caagtgcaag      420
tacccggagg gcaccaaggt gaccttccac gtggagaagg ggtccaaccc caactacctg     480
gcgctgcttg tgaagtacgt taacggcgac ggagacgtgg tggcggtgga catcgcggag     540
gcgggcgcgg acgcgtggat cgagctcaag gagtcgtggg gagccatctg gaggatcgac     600
actcccgaca agctcacggg ccccttcacc gtccgctaca ccaccgaggg cggcaccaag     660
accgaagccg aggacgtcat ccctgagggc tggaaggcca acaccagcta cgagtccaag     720
```

<210> SEQ ID NO 2
<211> LENGTH: 240
<212> TYPE: PRT
<213> ORGANISM: Phleum pratense

<400> SEQUENCE: 2

```
Ile Pro Lys Val Pro Pro Gly Pro Asn Ile Thr Ala Thr Tyr Gly Asp
 1               5                  10                  15

Lys Trp Leu Asp Ala Lys Ser Thr Trp Tyr Gly Ala Pro Thr Gly Ala
            20                  25                  30

Gly Pro Ala Asp Asn Gly Gly Ala Cys Gly Tyr Ala Asp Val Asp Ala
        35                  40                  45

Pro Pro Phe Ser Gly Met Thr Gly Cys Gly Asn Thr Pro Ile Phe Lys
    50                  55                  60

Ser Gly Arg Gly Cys Gly Ser Cys Phe Glu Ile Lys Cys Thr Lys Pro
65                  70                  75                  80

Glu Ala Cys Ser Gly Glu Pro Val Val Val His Ile Thr Asp Asp Asn
                85                  90                  95
```

```
Glu Glu Pro Ile Ala Pro Tyr His Phe Asp Leu Ser Gly His Ala Phe
            100             105             110

Gly Ala Met Ala Lys Lys Gly Asp Glu Gln Lys Leu Arg Ser Ala Gly
        115             120             125

Glu Leu Glu Leu Gln Phe Arg Arg Val Lys Cys Lys Tyr Pro Glu Gly
    130             135             140

Thr Lys Val Thr Phe His Val Glu Lys Gly Ser Asn Pro Asn Tyr Leu
145             150             155             160

Ala Leu Leu Val Lys Tyr Val Asn Gly Asp Gly Asp Val Val Ala Val
                165             170             175

Asp Ile Ala Glu Ala Gly Ala Asp Ala Trp Ile Glu Leu Lys Glu Ser
            180             185             190

Trp Gly Ala Ile Trp Arg Ile Asp Thr Pro Asp Lys Leu Thr Gly Pro
        195             200             205

Phe Thr Val Arg Tyr Thr Thr Glu Gly Gly Thr Lys Thr Glu Ala Glu
        210             215             220

Asp Val Ile Pro Glu Gly Trp Lys Ala Asp Thr Ser Tyr Glu Ser Lys
225             230             235             240
```

VARIANTS OF *PHLEUM PRATENSE* ALLERGENIC PROTEINS

The present invention relates to novel variants of an allergen of the pollen of plants of the species *Phleum pratense*.

More particularly, the present invention relates to the amino acidic sequences of hypoallergenic variants of the allergen Ph1 p 1, obtained by site-specific mutagenesis of the nucleotidic sequence encoding for said allergen. The hypoallergenic variants can be used in the specific immunotherapy of allergic pathologies caused by Graminaceae pollen.

BACKGROUND OF THE INVENTION

Graminaceae are the major cause of allergy in the Mediterranean area.

Thirteen different types of allergenic proteins, phylogenetically conserved within this family, have been identified in their pollen. For each allergen, the homologous proteins present in the various species constitute a class, inside which high cross-reactivity towards immunoglobulins E (IgE), the antibodies modulating the allergic response, is observed.

Classes 1 and 5 are formed by major allergens, i.e. the most clinically relevant allergens, in that IgEs to the components of these groups are present statistically in more than 80% of subjects allergic to Graminaceae.

*Phleum pratense*, a Graminacea widely diffused due to its value as fodder, is therefore extremely important from the allergological point of view.

The major allergen Ph1 p 1 of *Phleum pratense* (identified in GenBank under the accession code X78813) is a protein of 240 amino acids, which in vivo forms one of the components of cell wall (beta-expansin). This allergen has higher than 90% homology to the other class 1 proteins characterized up to now (1). One of the immunochemical properties that Ph1 p 1 shares with the other allergens of the same group is the presence of common epitopes for IgEs (2). As a consequence, the allergen Ph1 p 1 can be used for both the diagnosis and the therapy of the allergies to Graminaceae pollen caused by major allergens of class 1, independently of the species of origin.

The only etiological treatment of allergies is represented by specific hyposensitizing immunotherapy (SIT). This consists in administering increasing doses of the substance which causes the allergy, thus inducing gradual desensitization to said substance in the patient (3).

Immunotherapy may, however, induce even serious systemic effects, which restrict the use thereof (4).

Progresses in SIT, intended to ensure a more effective, safer treatment, include the use of mutagenized recombinant allergens having reduced allergenic activity (reactivity to IgEs) while maintaining unaffected their capability of inducing favourable immunological changes (5).

DETAILED DISCLOSURE OF THE INVENTION

Analysis of Ph1 p 1 structure (GenBank X78813, natural form disclosed as SEQ ID NO: 3, and mature form disclosed as SEQ ID NO: 4) and particularly of its hydrophilicity profile, allowed to identify the regions apparently responsible for the binding to IgEs. It has therefore been proved that that allergenic effect of Ph1 p 1 may be reduced by changing its amino acidic sequence in at least one of the positions n. 28, 35, 44, 48, 179, 181, 183, 185, in which a residue of the amino acid lysine is present. "Change" herein means substituting one or more residues in the specified positions preferably with neutral or polar amino acids, or deleting one or more Lys residues present in the natural form, or simultaneously substituting and deleting two or more residues.

The preferred mutations by substitution are those in which an alanine residue is inserted at each of the 8 positions indicated above. Most preferred is the variant in which the eight substitutions indicated in SEQ ID N. 2 are simultaneously present.

The present invention also comprises the class 1 allergenic proteins of Graminaceae having sequence homology higher than 85% compared with Ph1 p 1 and having, at the corresponding positions of the amino acidic sequence, the same substitution/deletion pattern as described above for Ph1 p 1.

The invention further comprises an immunologically active peptide deriving from the amino acidic sequence of Ph1 p 1, or from an homologous sequence thereof, and containing at least one of the substitutions/deletions described above.

In a further aspect, the invention is directed to a nucleic acid molecule encoding for a mutation variant of Ph1 p 1, for an homologous variant thereof, or for a peptide derived therefrom, as specified above.

The sequence variants according to the invention can easily be prepared starting from cDNA of the allergen Ph1 p 1 mature form, or of an homologous variant thereof, which does not include the region coding the signal peptide and suitably mutagenized at the desired positions.

The cDNA sequence (mutagenized bases in bold print) coding the preferred variant with the 8 substitutions corresponding to SEQ ID N. 2, is reported in SEQ ID N. 1.

Figure 1:
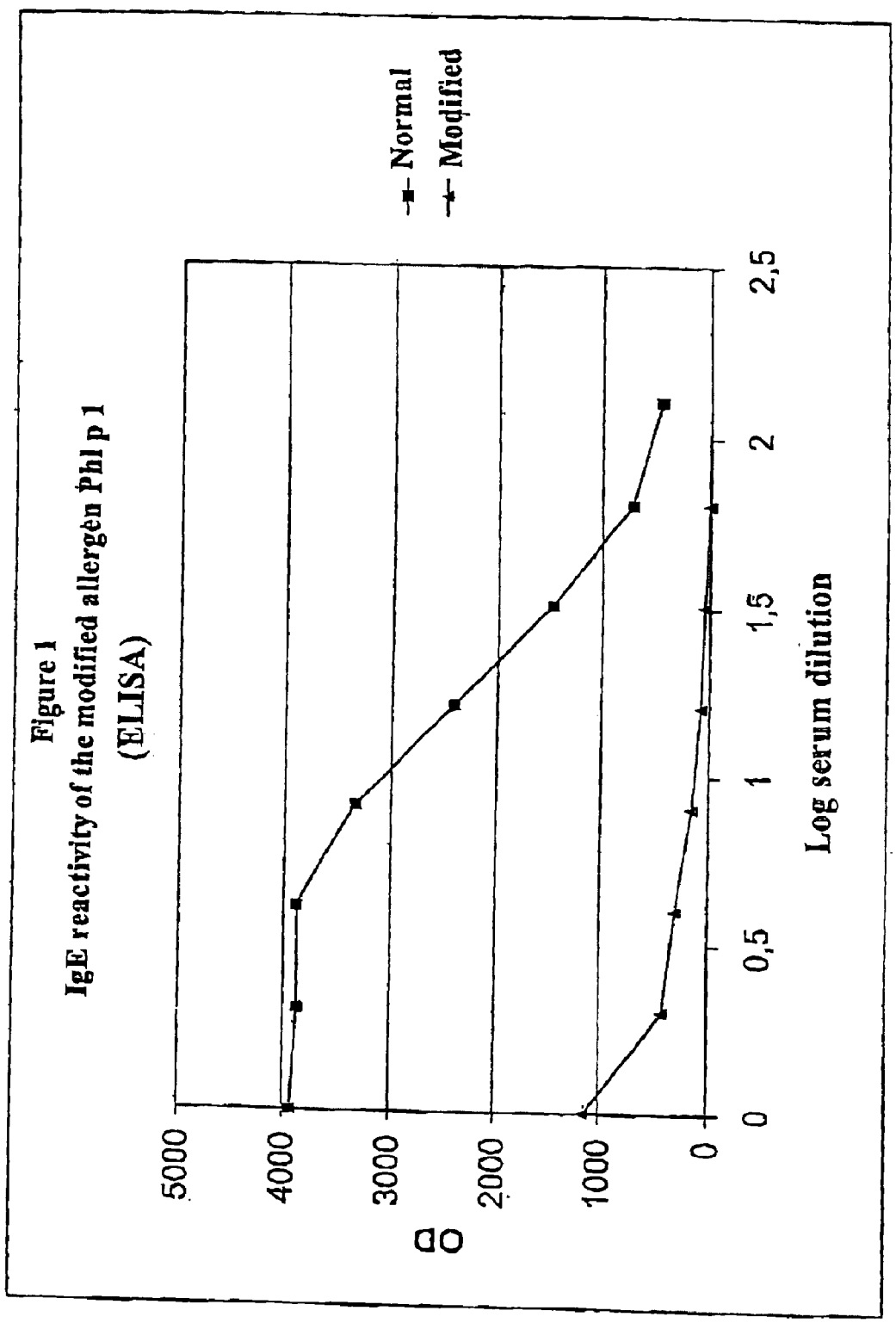
FIG. 1 shows the IgE reactivity of the modified allergen Ph1 p 1.
Figure 2:
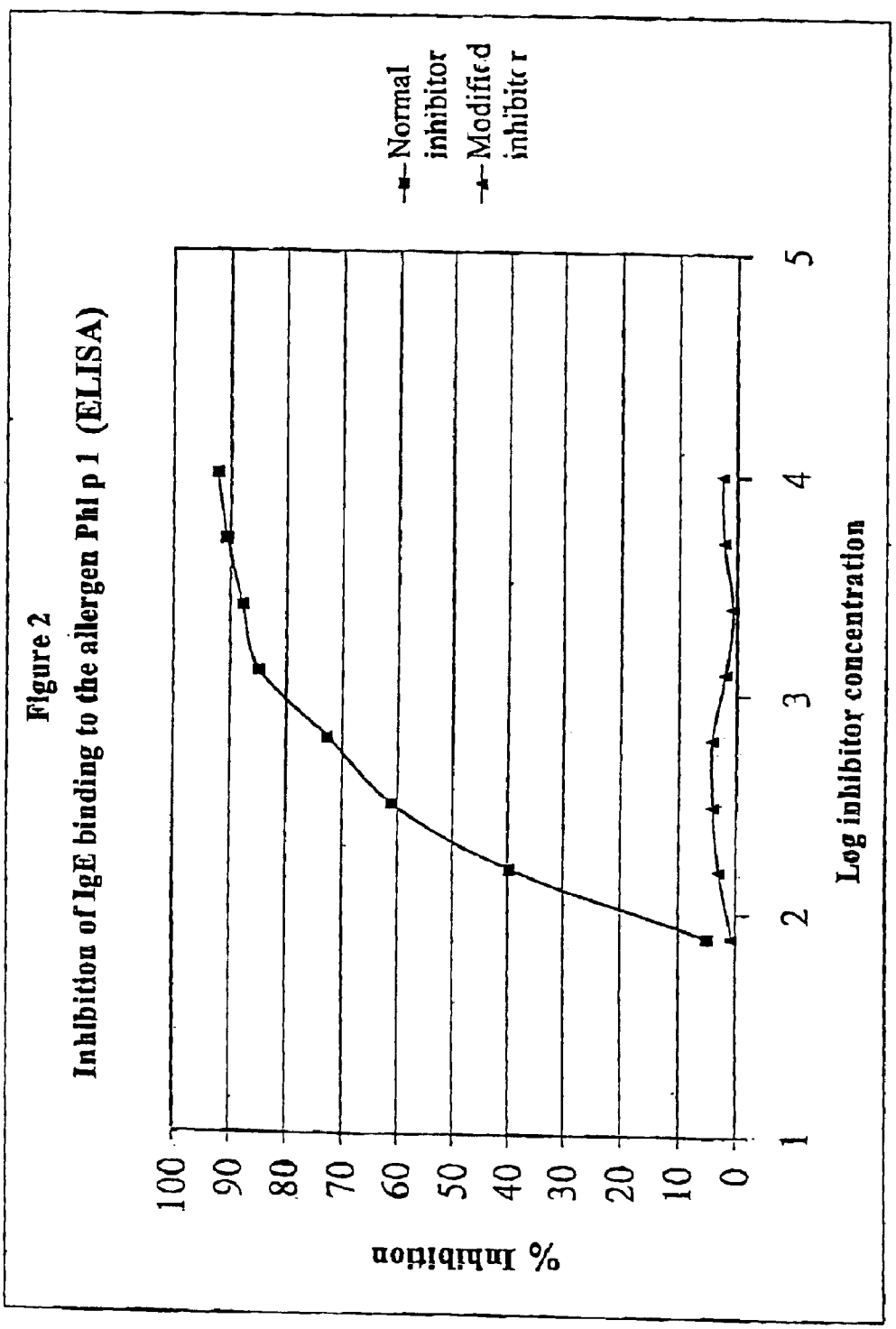
FIG. 2 shows inhibition of IgE binding to the allergen Ph1 p 1.

The cDNA of SEQ ID N. 1 was expressed in *Escherichia coli* cells. The produced recombinant protein has reduced IgE reactivity of the serum from subjects allergic to *Phleum pratense* pollen. In particular, ELISA immunoassays proved that IgE reactivity of the variant reported in SEQ ID N.2 decreases on the average by more than 95% compared with that of the normal protein produced in *Escherichia coli* [FIG. 1]. This result was confirmed by inhibition tests (indirect ELISA), which allowed to identify the same epitopes in different proteins. The binding of normal Ph1 p 1 protein to IgEs from a pool of RAST 5+sera is inhibited when serum is pretreated with this protein [FIG. 2, normal inhibitor]. When serum is preincubated with the modified protein reported in SEQ ID N. 2, inhibition of IgE binding to the normal allergen is lower than 5%, even at high concentrations of inhibitor [FIG. 2, modified inhibitor]. These results clearly prove that the epitopes of the allergen Ph1 p 1 able to bind IgEs are not present in the modified variant reported in SEQ ID N. 2.

The invention further relates to an expression vector comprising a nucleic acid molecule coding for any one of the hypoallergenic variants defined above.

Said vector can be a plasmid, cosmid, virus, bacteriophage or any other vector commonly used in genetic engineering, and can include, in addition to the nucleic acid molecule of the invention, eukaryotic or prokaryotic elements for the control of the expression, such as regulatory sequences for the initiation and the termination of the transcription, enhancers, promoters, signal sequences and the like.

Moreover, the invention comprises a prokaryotic or eukaryotic host cell transformed into or transfected with the vector of the invention. In principle, prokaryotic cells such as *Escherichia coli* or *Bacillus subtilis*, or eukaryotic cells such as *Saccharomyces cerevisiae* will be used for cloning the vector and expressing the cDNA.

The protein variants of the invention can be produced either as such or as fusion proteins.

Thanks to the reduced IgE reactivity, said variants may be used for therapeutical purposes in the preparation of vaccines to be used in the immunotherapy of allergies to Graminaceae pollen.

A further aspect of the invention relates therefore to a pharmaceutical composition comprising an effective amount of the hypoallergenic variant of the invention, optionally in combination with other natural or modified allergens of Graminaceae, together with pharmaceutically acceptable excipients.

In a preferred embodiment, said pharmaceutical composition is a vaccine for use in the prophylactic or therapeutical treatment of allergic diseases, such as bronchial asthma, allergic rhinitis, allergic dermatitis, allergic conjunctivitis. Vaccination principles and practice are well known to those skilled in the art and are described, for example, in (6) and (7).

The following examples illustrate the invention in greater detail.

EXAMPLES

The methods used in the following examples, if not otherwise specified, are those described by Sambrook, Fritsch E T Maniatis "Molecular cloning. A laboratory manual" II ed. vol. 1-2-3 CSH Lab Press 1989.

Example 1

Site-specific Mutagenesis of the cDNA Coding for the Allergen Ph1 p 1

The site-specific mutagenesis of the cDNA coding for the allergen Ph1 p 1 is carried out by PCR amplification (Polymerase Chain Reaction) of the same cDNA cloned in a prokaryotic vector (pBluescript).

The oligonucleotides used as primer for the PCR reaction have the required substitutions of bases. For each mutagenesis, a complementary pair of said oligonucleotides has been used, which bind to corresponding regions of the two DNA strands. After amplification, the original, unchanged template is selectively degraded by enzymatic digestion catalyzed by the restriction enzyme Dpn 1. *Escherichia coli* cells are then transformed with the mutagenized molecules. Clones obtained from single bacterial colonies are sequenced according to the Sanger method to verify the correct modification of the bases and the absence of cDNA aspecific mutations.

Example 2

Production of the Protein Ph1 p 1 and of the Variant Thereof

Normal cDNA from Ph1 p 1 and mutagenized cDNA, corresponding to SEQ ID N. 1, after cloning in an expression vector (pCALn—Stratagene), are expressed in *Escherichia coli* cells according to standard protocols, wherein the culture in esponential growth (O.D. 600 nm=0.6) is added with of IPTG (isopropyl-β-D-thiogalactopyranoside) for inducing the expression of cDNA. The recombinant proteins are isolated 2 hrs after induction of their synthesis by lysis of the bacterial cells through sonication and removal of cell particulate by centrifugation. Proteins are purified from supernatant by affinity chromatography, using columns wherein the matrix is bonded to the calmodulin protein, which interacts with the CBP portion (Calmodulin Binding Protein) fused to the allergen.

Example 3

ELISA Assay for IgE Reactivity of the Ph1 p 1 Variant

Equal amounts (0.1 µg) of normal allergen and of its mutagenized variants, in carbonate/bicarbonate 50 mM buffer, pH 9,6, are adsorbed on wells of polystyrene plates for ELISA tests by incubation at 4° C. for 16 hours. The antigens are then washed with washing solution (60 mM phosphate buffer pH 6,5 containing 0.05% Tween-20) and the free sites are saturated with diluent solution (25% horse serum, EDTA 1 mM, 0.05% Tween 20, 0.01% Thiomersal in phosphate buffer 150 mM pH 7,4). Serial dilutions of human serum pools with RAST 5+reactivity are prepared in a 1:2 ratio in diluent buffer. Equal amounts (100 µl) of the various serum dilutions are added to each sample and incubated at 25° C. for 2 hours. After three washings, the anti-human IgE peroxisase conjugated antiserum diluted 1:1500 in diluent buffer is added, and incubated at 25° C. for 1.5 hours. After three washings, the colorimetric reaction is developed by addition of 100 µl of Ultra Blu reagent (Intergen, Milford, Mass.) and incubation for 15 minutes at 25° C. The reaction is stopped by addition of 100 µl of 1N HCl and evaluated at 450 nm with a spectrophotometer.

Example 4

EAST Inhibition ELISA-inhibition Assay for IgE Reactivity of the Ph1 p 1 Variant An amount (0.1 µg) of the normal allergen Ph1 p 1 is adsorbed onto wells of ELISA plates and the free sites are saturates as indicated in Example 3. A suitable amount of a pool of human sera with RAST 5+reactivity to *Phleum pratense* pollen is incubated with different concentrations of inhibitor at 25° C. for 3 hours. Afterwards, an equal amount (0.1 ml) of serum is then added to each well. After incubation at 4° C. for 16 hours, 3 washings with 0.06 M phosphate buffer pH 6.5 containing 0.05% Tween-20 are carried out; then 0.1 ml of suitably diluted anti-human IgE peroxidatse conjugated antibody are added, incubating at 25° C. for 1.5 hours. After 3 washings, the colorimetric reaction is developed by addition of 0.1 ml of Ultra Blu reagent (Intergen, Milford, Mass.) to each well and incubation for 15 minutes at 25° C. The reaction is stopped by addition of 0.1 ml of 1N HCl and evaluated at 450 nm with a spectrophotometer.

The inhibition percentage is calculated by using the following formula: $100 \times [(A-B)/A]$, wherein A is the absorbance at 450 nm in the absence of inhibitor and B the absorbance in the presence of inhibitor.

References
1) Laffer S., Valenta R., Vrtala S., Susani M., van Ree R., Kraft D., Scheine O., Duchene M., (1994) "Complementary DNA cloning of the major allergen Ph1 p 1 from timothy grass (Phleum pratense); recombinant Phl p 1 inhibSHT IgE binding to group I allergens from eight different grass species". J. Allergy Clin. Immunol. 94 (4): 689–698
2) Laffer S., Duchene M., Reimitzer I., Susani M., Mannhalter C., Kraft D., Valenta R., (1996) "Common IgE-epitopes of recombinant Phl p 1, the major timothy grass pollen allergen and natural group I grass pollen isoallergens". Mol. Immunol. 33 (4–5): 417–426
3) Bousquet J., Lockey R., Malling H. J., (1998). "Allergen immunotherapy: therapeutic vaccines for allergic diseases. A WHO position paper". J. Allergy Clin. Immunol. 102 (4 Pt 1): 558–562
4) Karaayvaz M., Erel F., Caliskaner Z., Ozanguc N., (1999). "Systemic reactions two to allergen immunotherapy". J. Investig. Allergol. Clin. Immunol. 9 (1): 39–44
5) Ferreira F., Ebner C., Kramer B., Casari G., Briza P., Kungl A. J., Grimm R., Jahn-Schmid B., Breiteneder H., Kraft D., Breitenbach M., Rheinberger H. J., Scheiner O., (1998). "Modulation of IgE reactivity of allergens by site-directed mutagenesis: potential use of hypoallergenic variants for immunotherapy". FASEB J. 12: 231–242
6) Paul, (1989), "Fundamental Immunology", Raven press, New York.
7) Cryz, S. J. (1991), "Immunotherapy and Vaccines", VCH Verlagsgesellschaft.

What is claimed is:

1. A hypoallergenic protein of the major Ph1 p 1 allergen comprising an amino acid sequence that is homologous by 85% or more to SEQ ID NO. 4, and wherein there are substitutions and/or deletions of at least one of the lysine residues present at positions 28, 35, 44, 48, 179, 183 or 185 of said hypoallergenic protein, and wherein said hypoallergenic protein exhibits reduced IgE reactivity in serum from patients allergic to Phleum pratense pollen as compared to natural Ph1 p 1 allergen.

2. The protein as claimed in claim 1, wherein said residues are substituted with neutral or polar amino acids.

3. The protein as claimed in claim 1, wherein said residues are substituted with the amino acid alanine.

4. A protein comprising SEQ ID NO. 2.

5. A pharmaceutical composition comprising an effective amount of a protein as claimed in claim 1 together with pharmaceutically acceptable excipients.

6. A composition as claimed in claim 5, in the form of a vaccine.

7. A peptide comprising an immunologically active part of the protein of claim 6, wherein at least one of said lysine substitutions and/or deletions are present and wherein said peptide exhibits reduced IgE reactivity in serum from patients allergic to Phleum pratense pollen as compared to natural Ph1 p 1 allergen.

8. A pharmaceutical composition comprising an effective amount of a peptide as claimed in claim 7 together with pharmaceutically acceptable excipients.

* * * * *